US 7,485,761 B2

(12) United States Patent
Schindler et al.

(10) Patent No.: US 7,485,761 B2
(45) Date of Patent: *Feb. 3, 2009

(54) METHOD FOR PRODUCING 1-BUTENE

(75) Inventors: Götz-Peter Schindler, Mannheim (DE); Andreas Brodhagen, Dannstadt-Schauernheim (DE); Thorsten Johann, Limburgerhof (DE); Thomas Hill, Ludwigshafen (DE); Marcus Sigl, Ellerstadt (DE); Regina Benfer, Altrip (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 187 days.

This patent is subject to a terminal disclaimer.

(21) Appl. No.: 10/595,551

(22) PCT Filed: Oct. 27, 2004

(86) PCT No.: PCT/EP2004/012138

§ 371 (c)(1),
(2), (4) Date: Apr. 27, 2006

(87) PCT Pub. No.: WO2005/042449

PCT Pub. Date: May 12, 2005

(65) Prior Publication Data

US 2007/0055088 A1  Mar. 8, 2007

(30) Foreign Application Priority Data

Oct. 27, 2003  (DE) ................. 103 50 044

(51) Int. Cl.
*C07C 5/333*  (2006.01)

(52) U.S. Cl. ................. 585/325; 585/616; 585/621; 585/628; 585/629

(58) Field of Classification Search ................. 585/325, 585/616, 621, 628, 629
See application file for complete search history.

(56) References Cited

U.S. PATENT DOCUMENTS

| | | | |
|---|---|---|---|
| 3,161,670 A | 12/1964 | Adams et al. | |
| 4,408,085 A | 10/1983 | Gottlieb et al. | |
| 4,558,168 A | 12/1985 | Gussow et al. | |
| 4,718,986 A | 1/1988 | Comiotto et al. | |
| 4,788,371 A | 11/1988 | Imai et al. | |
| 4,902,849 A | 2/1990 | McKay et al. | |
| 4,996,387 A | 2/1991 | Gerhold et al. | |
| 4,996,849 A | 3/1991 | Burst et al. | |
| 5,087,780 A | 2/1992 | Arganbright | |
| 5,220,091 A | 6/1993 | Brinkmeyer et al. | |
| 5,389,342 A | 2/1995 | Savage et al. | |
| 5,430,220 A | 7/1995 | Khare et al. | |
| 5,877,369 A | 3/1999 | Wu et al. | |
| 5,955,640 A | 9/1999 | Paludetto et al. | |
| 6,414,209 B1 | 7/2002 | Herskowitz et al. | |
| 6,437,206 B1 | 8/2002 | Meyer et al. | |
| 6,670,303 B1 | 12/2003 | Heineke et al. | |
| 7,034,195 B2 | 4/2006 | Schindler et al. | |
| 2003/0220530 A1* | 11/2003 | Boelt et al. | ................. 585/648 |
| 2005/0119515 A1 | 6/2005 | Machhammer et al. | |
| 2005/0171311 A1 | 8/2005 | Schindler et al. | |

FOREIGN PATENT DOCUMENTS

| | | |
|---|---|---|
| DE | 199 37 105 | 2/2001 |
| DE | 199 37 106 | 2/2001 |
| DE | 199 37 107 | 2/2001 |
| DE | 102 11 275 | 9/2003 |
| EP | 0 117 146 | 8/1984 |
| EP | 0 992 284 | 4/2000 |
| GB | 628 686 A | 9/1949 |
| GB | 2 018 815 | 10/1979 |
| WO | WO-99/29420 | 6/1999 |
| WO | WO-99/46039 A1 | 9/1999 |
| WO | WO-2004/063656 | 7/2004 |

OTHER PUBLICATIONS

Sannfilippo, et al. "Fluidized Bed Reactors For Parraffins Dehydrogenation", Chemical Engineering Science, vol. 47, No. 9-11, pp. 2313-2318, 1992.

* cited by examiner

*Primary Examiner*—Thuan Dinh Dang
(74) *Attorney, Agent, or Firm*—Connolly Bove Lodge & Hutz LLP

(57) ABSTRACT

A process for preparing 1-butene, which includes nonoxidatively, catalytically dehydrogenating n-butane to obtain a product gas stream of n-butane, 1-butene, 2-butene, butadiene, hydrogen, and secondary constituents; removing hydrogen and the secondary constituents to obtain a $C_4$ product gas stream; separating the $C_4$ product stream into a recycle stream of n-butane and a stream of 1-butene, 2-butene and butadiene by extractive distillation, and recirculating the recycle stream to the dehydrogenation zone; introducing the 1-butene, 2-butene and butadiene stream into a selective hydrogenation zone and selective hydrogenation of butadiene to 1-butene and/or 2-butene to obtain a stream of 1-butene and 2-butene; introducing the 1-butene and 2-butene stream, and a circulating stream of 1-butene and 2-butene into a distillation zone and isolation of a product stream; and introducing the 2-butene-containing stream into an isomerization zone to obtain a circulating stream of 1-butene and 2-butene, and recirculating the circulating stream to the distillation zone.

7 Claims, No Drawings

METHOD FOR PRODUCING 1-BUTENE

CROSS REFERENCE TO RELATED APPLICATIONS

This application is a National Stage entry under 35 U.S.C. § 371 of PCT/EP2004/012138 filed on Oct. 27, 2004. International application PCT/EP2004/012138 claims priority to German application 103 50 044.8 filed on Oct. 27, 2003, the entire of contents of which is incorporated by reference herein.

The invention relates to a process for preparing 1-butene.

Butenes can be prepared by thermal dissociation (steam cracking) of saturated hydrocarbons, customarily using naphtha as raw material. Steam cracking of naphtha produces a hydrocarbon mixture comprising methane, ethane, ethene, acetylene, propane, propene, propyne, allene, butenes, butadiene, butynes, methylallene, $C_5$-hydrocarbons and higher hydrocarbons.

A disadvantage of the production of butene by cracking is that relatively large amounts of ethene or propene are inevitably formed as coproducts.

As an alternative, butenes can be prepared from n-butane by catalytic dehydrogenation. However, this process has the disadvantage that the catalytic hydrogenation of n-butane forms 2-butene and butadiene in relatively large amounts in addition to 1-butene.

It is an object of the invention to provide a process for preparing 1-butene from 1-butane, in which coproducts are formed to a very small extent.

This object is achieved by a process for preparing 1-butene from 1-butane, which comprises the steps A) provision of an n-butane-containing feed gas stream a;
B) introduction of the n-butane-containing feed gas stream a into at least one dehydrogenation zone and nonoxidative catalytic dehydrogenation of n-butane to give a product gas stream b comprising n-butane, 1-butene, 2-butene, butadiene, low-boiling secondary constituents, hydrogen and possibly water vapor;
C) removal of hydrogen, the low-boiling secondary constituents and, if appropriate, water vapor to give a $C_4$ product gas stream c consisting essentially of n-butane, 1-butene, 2-butene and butadiene;
D) separation of the $C_4$ product gas stream c into a recycle stream d1 consisting essentially of n-butane and a stream d2 comprising 1-butene, 2-butene and butadiene by extractive distillation and recirculation of the recycle stream d1 consisting essentially of n-butane to the dehydrogenation zone;
E) introduction of the stream d2 comprising 1-butene, 2-butene and butadiene into a selective hydrogenation zone and selective hydrogenation of butadiene to 1-butene and/or 2-butene to give a stream e comprising 1-butene and 2-butene;
F) introduction of the stream e comprising 1-butene and 2-butene and a circulating stream g comprising 1-butene and 2-butene into a distillation zone and isolation of a desired product stream f1 consisting essentially of 1-butene to leave a 2-butene-containing stream f2;
G) introduction of the 2-butene-containing stream f2, if appropriate after a purge gas stream has been separated off, into an isomerization zone and isomerization of 2-butene to 1-butene so as to give a circulating stream g comprising 1-butene and 2-butene and recirculation, if appropriate after a purge gas stream has been separated off from the circulating gas stream g, of the circulating gas stream g to the distillation zone.

The process of the invention makes particularly effective use of the raw materials. Thus, losses of the raw material n-butane are minimized by recirculation of unreacted n-butane to the dehydrogenation. n-Butane is virtually completely reacted in this way. Butadiene formed in the dehydrogenation is converted into further product of value by selective hydrogenation, and 2-butene formed in the dehydrogenation or the selective hydrogenation is converted by isomerization into desired product. Thus, neither butadiene nor 2-butene is obtained as coproduct. Furthermore, the formation of ethene and propene is minimized compared to steam cracking as a result of the higher selectivity of the nonoxidative butane dehydrogenation.

In a first part A of the process, an n-butane-containing feed gas stream a is provided. n-Butane-rich gas mixtures such as liquefied petroleum gas (LPG) are usually used as raw material for this purpose. LPG consists essentially of $C_2$-$C_5$-hydrocarbons. In addition, it contains methane and traces of $C_6^+$-hydrocarbons. The composition of LPG can fluctuate widely. The LPG used advantageously contains at least 10% by weight of butanes.

As an alternative, an upgraded $C_4$ stream from crackers or refineries can be used.

In a variant of the process of the invention, the provision of the n-butane-containing dehydrogenation feed gas stream comprises the steps A1) provision of a liquefied petroleum gas (LPG) stream,
A2) removal of propane and, if appropriate, methane, ethane and $C_5^+$-hydrocarbons (mainly pentanes, and also hexanes, heptanes, benzene and toluene) from the LPG stream to give a stream comprising butanes (n-butane and isobutane),
A3) removal of isobutane from the stream comprising butanes to give the n-butane-containing feed gas stream and, if appropriate, isomerization of the isobutane which has been separated off to form an n-butane/isobutane mixture and recirculation of the n-butane/isobutane mixture to the isobutane removal.

The removal of propane and, if appropriate, methane, ethane and $C_5^+$-hydrocarbons is carried out, for example, in one or more customary rectification columns. For example, low boilers (methane, ethane, propane) can be separated off overhead in a first column and high boilers ($C_5^+$-hydrocarbons) can be separated off at the bottom of a second column. This gives a stream comprising butanes (n-butane and isobutane) from which the isobutane is removed, for example, in a customary rectification column. The remaining, n-butane-containing stream is used as feed gas stream for the subsequent butane dehydrogenation.

The isobutane stream which has been separated off is preferably subjected to an isomerization. For this purpose, the isobutane-containing stream is fed into an isomerization reactor. The isomerization of isobutane to n-butane can be carried out as described in GB-A 2 018 815. This gives an n-butane/isobutane mixture which is fed into the n-butane/isobutane separation column.

The isobutane stream which has been separated off can also be passed to a further use, for example for preparing methacrylic acid, polyisobutene and methyl tert-butyl ether.

In a part B of the process, the n-butane-containing feed gas stream is fed into a dehydrogenation zone and subjected to a nonoxidative catalytic dehydrogenation. Here, n-butane is partially dehydrogenated over a dehydrogenation-active catalyst in a dehydrogenation reactor to form 1-butene and 2-butene, with butadiene also being formed. In addition, hydrogen and small amounts of methane, ethane, ethene, propane and propene are also obtained. Depending on the way in which the dehydrogenation is carried out, carbon oxides (CO, $CO_2$), water and nitrogen can also be present in the product gas mixture from the nonoxidative catalytic n-butane dehydrogenation. In addition, unreacted n-butane is present in the product gas mixture.

The nonoxidative catalytic n-butane dehydrogenation can be carried out with or without an oxygen-containing gas as cofeed.

A feature of the nonoxidative mode of operation compared to an oxidative mode of operation is the presence of hydrogen in the output gas. In oxidative dehydrogenation, free hydrogen is not formed in significant amounts.

The nonoxidative catalytic n-butane dehydrogenation can in principle be carried out in all reactor types and by all methods known from the prior art. A comparatively comprehensive description of dehydrogenation processes which are suitable for the purposes of the invention may be found in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

A suitable type of reactor is a fixed-bed tube reactor or a shell-and-tube reactor. In these, the catalyst (dehydrogenation catalyst and, when oxygen is employed as cofeed, optionally a specific oxidation catalyst) is present as a fixed bed in a reaction tube or in a bundle of reaction tubes. The reaction tubes are usually heated indirectly by a gas, e.g. a hydrocarbon such as methane, being burned in the space surrounding the reaction tubes. It is advantageous to apply this indirect form of heating only to the first about 20-30% of the length of the fixed bed and to heat the remaining length of the bed to the required reaction temperature by the radiant heat given off from the indirect heating. Customary internal diameters of the reaction tubes are from about 10 to 15 cm. A typical shell-and-tube reactor for dehydrogenation has from about 300 to 1000 reaction tubes. The temperature in the interior of the reaction tubes is usually in the range from 300 to 1200° C., preferably in the range from 500 to 1000° C. The working pressure is usually from 0.5 to 8 bar, frequently from 1 to 2 bar when using a low level of steam dilution (as in the Linde process for the dehydrogenation of propane) but can also be in the range from 3 to 8 bar when using a high level of steam dilution (as in the Phillips Petroleum Company's "steam active reforming process" (STAR process) for the dehydrogenation of propane or butane, cf. U.S. Pat. No. 4,902,849, U.S. Pat. No. 4,996,387 and U.S. Pat. No. 5,389,342). Typical GHSVs over the catalyst are from 500 to 2000 $h^{-1}$, based on hydrocarbon used. The catalyst geometry can, for example, be spherical or cylindrical (hollow or solid).

The nonoxidative catalytic n-butane dehydrogenation can also be carried out over a heterogeneous catalyst in a fluidized bed, as described in Chem. Eng. Sci. 1992 b, 47 (9-11) 2313. It is advantageous for two fluidized beds to be operated side by side, with one of these generally being regenerated at any given time. The working pressure is typically from 1 to 2 bar, and the dehydrogenation temperature is generally from 550 to 600° C. The heat required for the dehydrogenation is introduced into the reaction system by the dehydrogenation catalyst being preheated to the reaction temperature. When an oxygen-containing cofeed is mixed in, the preheaters can be omitted and the heat required can be generated directly in the reactor system by combustion of hydrogen and/or hydrocarbons in the presence of oxygen. If appropriate, a hydrocarbon-containing cofeed can additionally be mixed in.

The nonoxidative catalytic n-butane dehydrogenation can be carried out with or without an oxygen-containing gas as cofeed in a tray reactor. This comprises one or more successive catalyst beds. The number of catalyst beds can be from 1 to 20, advantageously from 1 to 6, preferably from 1 to 4 and in particular from 1 to 3. The reaction gas preferably flows radially or axially through the catalyst beds. In general, such a tray reactor is operated using one fixed bed of catalyst. In the simplest case, the fixed beds of catalyst are arranged axially or in the annular gaps between concentric cylindrical meshes in a shaft furnace reactor. One shaft furnace reactor corresponds to one tray. Carrying out the dehydrogenation in a single shaft furnace reactor corresponds to a preferred embodiment, with an oxygen-containing cofeed being able to be employed. In a further preferred embodiment, the dehydrogenation is carried out in a tray reactor having 3 catalyst beds. When the reactor is operated without an oxygen-containing gas as cofeed, the reaction gas mixture is subjected to intermediate heating in the tray reactor on its way from one catalyst bed to the next catalyst bed, e.g. by passing it over heat exchanger surfaces heated by means of hot gases or by passing it through tubes heated by means of hot combustion gases.

In a preferred embodiment of the process of the invention, the nonoxidative catalytic n-butane dehydrogenation is carried out autothermally. For this purpose, oxygen is additionally mixed into the reaction gas mixture of the n-butane dehydrogenation in at least one reaction zone and the hydrogen and/or hydrocarbon present in the reaction gas mixture is at least partly burnt to generate at least part of the required heat of dehydrogenation directly in the reaction gas mixture in the reaction zone or zones.

In general, the amount of oxygen-containing gas added to the reaction gas mixture is chosen so that the combustion of hydrogen present in the reaction gas mixture and, if appropriate, of hydrocarbons present in the reaction gas mixture and/or of carbon present in the form of carbon deposits generates the quantity of heat necessary for the dehydrogenation of the n-butane. In general, the total amount of oxygen introduced is, based on the total amount of butane, from 0.001 to 0.5 mol/mol, preferably from 0.005 to 0.2 mol/mol, particularly preferably from 0.05 to 0.2 mol/mol. Oxygen can be used either as pure oxygen or as oxygen-containing gas in admixture with inert gases, for example in the form of air. The inert gases and the resulting combustion gases generally have an additional diluting effect and thus promote the heterogeneously catalyzed dehydrogenation.

The hydrogen which is burnt to generate heat is the hydrogen formed in the catalytic n-butane dehydrogenation and also any hydrogen which is additionally added as hydrogen-containing gas to the reaction gas mixture. The amount of hydrogen present should preferably be such that the molar ratio of $H_2/O_2$ in the reaction gas mixture immediately after the introduction of oxygen is from 1 to 10 mol/mol, preferably from 2 to 5 mol/mol. In the case of multistage reactors, this applies to each intermediate introduction of oxygen-containing and, if applicable, hydrogen-containing gas.

The combustion of hydrogen occurs catalytically. The dehydrogenation catalyst used generally also catalyzes the combustion of hydrocarbons and of hydrogen in the presence of oxygen, so that a different, specific oxidation catalyst is in principle not necessary. In one embodiment, the dehydrogenation is carried out in the presence of one or more oxidation catalysts which selectively catalyze the combustion of hydrogen to oxygen in the presence of hydrocarbons. The combustion of these hydrocarbons in the presence of oxygen to form CO, $CO_2$ and water therefore proceeds to only a minor extent. The dehydrogenation catalyst and the oxidation catalyst are preferably present in different reaction zones.

When the reaction is carried out in a plurality of stages, the oxidation catalyst can be present in only one reaction zone, in a plurality of reaction zones or in all reaction zones.

The catalyst which selectively catalyzes the oxidation of hydrogen is preferably located at places where the prevailing oxygen partial pressures are higher than at other places in the reactor, in particular in the vicinity of the feed point for the oxygen-containing gas. Oxygen-containing gas and/or hydrogen-containing gas can be introduced at one or more points on the reactor.

In one embodiment of the process of the invention, oxygen-containing gas and hydrogen-containing gas are introduced intermediately upstream of each tray of a tray reactor. In a further embodiment of the process of the invention, oxygen-containing gas and hydrogen-containing gas are introduced upstream of each tray apart from the first tray. In one embodiment, a layer of a specific oxidation catalyst is present downstream of each point of introduction, followed by a layer of the dehydrogenation catalyst. In a further embodiment, no specific oxidation catalyst is present. The dehydrogenation temperature is generally from 400 to 1100° C., and the pressure in the last catalyst bed of the tray reactor is generally from 0.2 to 5 bar, preferably from 1 to 3 bar. The throughput (GHSV) is generally from 500 to 2000 $h^{-1}$, and in the case of high-load operation can also be up to 100 000 $h^{-1}$, preferably from 4000 to 16 000 $h^{-1}$.

A preferred catalyst which selectively catalyzes the combustion of hydrogen comprises oxides and/or phosphates selected from the group consisting of the oxides and phosphates of germanium, tin, lead, arsenic, antimony or bismuth. A further preferred catalyst which catalyzes the combustion of hydrogen comprises a noble metal of transition groups VIII and/or I.

The dehydrogenation catalysts used generally comprise a support and an active composition. The support generally comprises a thermally stable oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof as support. In the case of mixtures, these can be physical mixtures or chemical mixed phases such as magnesium-aluminum or zinc-aluminum mixed oxides. Preferred supports are zirconium dioxide and/or silicon dioxide, and particular preference is given to mixtures of zirconium dioxide and silicon dioxide.

The active composition of the dehydrogenation catalysts generally comprises one or more elements of transition group VIII, preferably platinum and/or palladium, particularly preferably platinum. In addition, the dehydrogenation catalysts can comprise one or more elements of main groups I and/or II, preferably potassium and/or cesium. Furthermore, the dehydrogenation catalysts can comprise one or more elements of transition group III including the lanthanides and actinides, preferably lanthanum and/or cerium. Finally, the dehydrogenation catalysts can comprise one or more elements of main groups III and/or IV, preferably one or more elements selected from the group consisting of boron, gallium, silicon, germanium, tin and lead, particularly preferably tin.

In a preferred embodiment, the dehydrogenation catalyst comprises at least one element of transition group VIII, at least one element of main groups I and/or II, at least one element of main groups III and/or IV and at least one element of transition group III including the lanthanides and actinides.

For example, all dehydrogenation catalysts disclosed in WO 99/46039, U.S. Pat. No. 4,788,371, EP-A 705 136, WO 99/29420, U.S. Pat. No. 5,220,091, U.S. Pat. No. 5,430,220, U.S. Pat. No. 5,877,369, EP 0 117 146, DE-A 199 37 106, DE-A 199 37 105 and DE-A 199 37 107 can be used according to the invention. Particularly preferred catalysts for the above-described variants of autothermal n-butane dehydrogenation are the catalysts described in examples 1, 2, 3 and 4 of DE-A 199 37 107.

The n-butane dehydrogenation is preferably carried out in the presence of water vapor. The added water vapor serves as heat carrier and aids the gasification of organic deposits on the catalysts, as a result of which the formation of carbon deposits on the catalysts is countered and the operating life of the catalysts is increased. The organic deposits are in this case converted into carbon monoxide, carbon dioxide and possibly water.

The dehydrogenation catalyst can be regenerated in a manner known per se. Thus, water vapor can be added to the reaction gas mixture or an oxygen-containing gas can be passed at elevated temperature over the catalyst bed from time to time so as to burn off the deposited carbon. The dilution with water vapor shifts the equilibrium in the direction of the products of the dehydrogenation. If appropriate, the catalyst is reduced by means of a hydrogen-containing gas after regeneration.

The n-butane dehydrogenation gives a gas mixture which comprises butadiene, 1-butene, 2-butene and unreacted n-butane together with secondary constituents. The usual secondary constituents are hydrogen, water vapor, nitrogen, CO and $CO_2$, methane, ethane, ethene, propane and propene. The composition of the gas mixture leaving the first dehydrogenation zone can vary widely depending on the way in which the dehydrogenation is carried out. Thus, when the preferred autothermal dehydrogenation with introduction of oxygen and additional hydrogen is carried out, the product gas mixture has a comparatively high content of water vapor and carbon oxides. In modes of operation without introduction of oxygen, the product gas mixture of the nonoxidative dehydrogenation has a comparatively high hydrogen content.

The product gas stream from the nonoxidative autothermal n-butane dehydrogenation typically comprises from 0.1 to 15% by volume of butadiene, from 1 to 15% by volume of 1-butene, from 1 to 25% by volume of 2-butene (cis/trans-2-butene), from 20 to 70% by volume of n-butane, from 1 to 70% by volume of water vapor, from 0 to 10% by volume of low-boiling hydrocarbons (methane, ethane, ethene, propane and propene), from 0.1 to 40% by volume of hydrogen, from 0 to 70% by volume of nitrogen and from 0 to 5% by volume of carbon oxides.

In a part C of the process, the low-boiling secondary constituents other than the $C_4$-hydrocarbons (n-butane, isobutane, 1-butene, cis-/trans-2-butene, isobutene, butadiene) are at least partly but preferably essentially completely removed from the product gas stream from the n-butane dehydrogenation to give a $C_4$ product gas stream c.

The product gas stream b leaving the dehydrogenation zone is preferably divided into two substreams and only one of the two substreams is subjected to the further parts C to G of the process while the second substream is recirculated to the dehydrogenation zone. An appropriate mode of operation is described in DE-A 102 11 275. However, it is also possible for the entire product gas stream b from the n-butane dehydrogenation to be subjected to the further parts C to G of the process.

In one embodiment of the process of the invention, water is firstly separated off from the product gas stream b in part C of the process. The removal of water can, for example, be effected by condensation by cooling and/or compression of the product gas stream b and can be carried out in one or more cooling and/or compression stages. The water removal is usually carried out when the n-butane dehydrogenation is carried out autothermally or isothermally with introduction of water vapor (as in the Linde or STAR process for the dehydrogenation of propane) and the product gas stream b consequently has a high water content.

The low-boiling secondary constituents can be separated off from the product gas stream by conventional separation methods such as distillation, rectification, membrane processes, absorption or adsorption.

To separate off the hydrogen present in the product gas stream b from the n-butane dehydrogenation, the product gas mixture can, if appropriate after cooling, for example in an indirect heat exchanger, be passed over a membrane which is permeable only to molecular hydrogen and is generally configured as a tube. The molecular hydrogen which has been separated off in this way can if necessary be at least partly used in the dehydrogenation or else can be passed to another use, for example for the generation of electric energy in fuel cells.

The carbon dioxide present in the product gas stream b from the dehydrogenation can be removed by means of a $CO_2$ gas scrub. The carbon dioxide gas scrub can be preceded by a separate combustion stage in which carbon monoxide is selectively oxidized to carbon dioxide.

In a preferred embodiment of the process of the invention, the incondensable or low-boiling gas constituents such as hydrogen, carbon oxides, the low-boiling hydrocarbons (methane, ethane, ethene, propane, propene) and if applicable nitrogen are separated off in an absorption/desorption cycle using a high-boiling absorption medium to give a $C_4$ product gas stream c which consists essentially of the $C_4$-hydrocarbons. In general, the $C_4$ product gas stream c comprises at least 80% by volume, preferably at least 90% by volume, particularly preferably at least 95% by volume, of the $C_4$-hydrocarbons.

For this purpose, the product gas stream b is, if appropriate after prior water removal, brought into contact with an inert absorption medium in an absorption stage and the $C_4$-hydrocarbons are absorbed in the inert absorption medium, giving an absorption medium laden with $C_4$-hydrocarbons and an offgas containing the other gas constituents. In a desorption stage, the $C_4$-hydrocarbons are liberated again from the absorption medium.

Inert absorption media used in the absorption stage are generally high-boiling nonpolar solvents in which the $C_4$-hydrocarbon mixture to be separated off is significantly more soluble than are the remaining gas constituents to be removed. The absorption can be carried out by simply passing the product gas stream b through the absorption medium. However, it can also be carried out in columns or in rotary absorbers. It can be carried out in cocurrent, countercurrent or crosscurrent. Suitable absorption columns are, for example, tray columns having bubble cap trays, centrifugal trays and/or sieve trays, columns containing structured packing, e.g. sheet metal packing having a specific surface area of from 100 to 1000 $m^2/m^3$, e.g. Mellapak® 250 Y, and columns containing random packing. It is also possible to use trickle towers and spray towers, graphite block absorbers, surface absorbers such as thick film and thin film absorbers and also rotary columns, pan scrubbers, cross-spray scrubbers and rotary scrubbers.

Suitable absorption media are comparatively nonpolar organic solvents, for example, aliphatic $C_8$-$C_{18}$-alkenes or aromatic hydrocarbons such as middle oil fractions from paraffin distillation or ethers having bulky groups, or mixtures of these solvents, with a polar solvent such as 1,2-dimethyl phthalate being able to be added to these. Further suitable absorption media are esters of benzoic acid and phthalic acid with straight-chain $C_1$-$C_8$-alkanols, e.g. n-butyl benzoate, methyl benzoate, ethyl benzoate, dimethyl phthalate, diethyl phthalate, and also heat transfer oils such as biphenyl and diphenyl ether, their chlorinated derivatives and also triarylalkenes. One suitable absorption medium is a mixture of biphenyl and diphenyl ether, preferably a mixture having the azeotropic composition, for example the commercially available Diphyl®. This solvent mixture frequently contains from 0.1 to 25% by weight of dimethyl phthalate. Other suitable absorption media are octanes, nonanes, decanes, undecanes, dodecanes, tridecanes, tetradecanes, tetradecanes, pentadecanes, hexadecanes, heptadecanes and octadecanes and fractions which are obtained from refinery streams and comprise the linear alkanes mentioned as main components.

To desorb the $C_4$-hydrocarbons, the laden absorption medium is heated and/or depressurized to a lower pressure. As an alternative, the desorption can also be effected by stripping or in a combination of depressurization, heating and stripping in one or more process steps. The absorption medium which has been regenerated in the desorption stage is recirculated to the absorption stage.

In one process variant, the desorption step is carried out by depressurization and/or heating of the laden desorption medium.

The separation C is generally not absolutely complete, so that, depending on the way in which the separation is carried out, small amounts or even only traces of the further gas constituents, in particular the low-boiling hydrocarbons, can still be present in the $C_4$ product gas stream.

The reduction in volume flow which is also effected by the separation C reduces the load on the subsequent process steps.

The $C_4$ product gas stream C consisting essentially of n-butane, 1-butene, 2-butene and butadiene generally comprises from 20 to 80% by volume of n-butane, from 5 to 40% by volume of 1-butene, from 10 to 50% by volume of 2-butene and from 0 to 30% by volume of butadiene.

In a part D of the process, the $C_4$ product gas stream c is separated by means of extractive distillation into a recycled stream d1 consisting essentially of n-butane and a stream d2 comprising 1-butene, 2-butene, butadiene and n-butane. For this purpose, the $C_4$ product gas stream c is brought into contact with an extractant, preferably an N-methylpyrrolidone (NMP)/water mixture, in an extraction zone in which the butenes and butadiene are absorbed essentially completely but the butanes (n-butane and isobutane) remain essentially in the gas phase. The extraction zone is generally configured as a scrubbing column containing trays, random packing or ordered packing as internals. This generally has from 30 to 70 theoretical plates so that a sufficiently good separation action is achieved. The scrubbing column preferably has a backscrubbing zone at the top of the column. This backscrubbing zone serves to recover the NMP present in the gas phase by means of liquid hydrocarbon runback, for which purpose the overhead fraction is condensed beforehand. Typical temperatures at the top of the column are from 30 to 60° C. The mass ratio of NMP to $C_4$ product gas stream c in the feed to the extraction zone is generally from 10:1 to 20:1.

Suitable extractants are butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, in particular N-methylpyrrolidone (NMP). In general, alkyl-substituted lower aliphatic acid amides or N-alkyl-substituted cyclic acid amides are used. Dimethylformamide, acetonitrile, furfural and, in particular, NMP are particularly advantageous.

However, it is also possible to use mixtures of these extractants with one another, e.g. mixtures of NMP and acetonitrile, mixtures of these extractants with cosolvents and/or tert-butyl ethers, e.g. methyl tert-butyl ether, ethyl tert-butyl ether, propyl tert-butyl ether, n-butyl or isobutyl tert-butyl ether. NMP is particularly useful, preferably in aqueous solution, more preferably with from 0 to 20% by weight of water, particularly preferably with from 7 to 10% by weight of water, in particular with 8.3% by weight of water.

In the extraction zone, a gaseous butane stream d1 and an extraction solution comprising butenes and butadiene are formed. The gaseous butanes stream d1 is recirculated as recycled stream d1 to the n-butane dehydrogenation zone. In general, the recycled stream d1 consisting essentially of n-butane comprises from 82 to 99% by volume of n-butane, from 1 to 15% by volume of butenes and from 0 to 3% by volume of further constituents such as butadiene and isobutane.

The extraction solution is transferred to a desorption zone at a pressure which is lower than in the extraction zone and/or a temperature which is higher than in the extraction zone and the butenes and butadiene are desorbed from the extraction solution. The desorption zone can, for example, be configured as a scrubbing column having from 5 to 15, preferably from 8 to 10, theoretical plates and a backscrubbing zone having, for example, 4 theoretical plates. This backscrubbing zone serves to recover the NMP present in the gas phase by means of liquid hydrocarbon runback, for which purpose the overhead fraction is condensed beforehand. Ordered packing, trays or random packing is/are provided as internals. The pressure at the top of the column is, for example 1.5 bar. The temperature at the bottom of the column is, for example, from 130 to 150° C. The stream d2 obtained at the top of the column generally comprises from 0 to 10% by volume of n-butane, from 20 to 60% by volume of 1-butene, from 40 to 80% by volume of 2-butene and from 0 to 50% by volume of butadiene.

In a part E of the process, the stream d2 comprising predominantly 1-butene, 2-butene and butadiene is fed into a selective hydrogenation zone and a selective hydrogenation of butadiene to 1-butene and/or 2-butene is carried out.

The volume flow minimization effected by the removal of the secondary constituents decreases the load on the subsequent stages of the process.

In a part D of the process, the $C_4$ product gas stream c consisting essentially of n-butane, 1-butene, 2-butene and butadiene is introduced into a selective hydrogenation zone and a selective hydrogenation of butadiene to 1-butene and/or 2-butene is carried out.

The selective hydrogenation can be carried out in a manner known per se in the gas phase, liquid phase or trickle phase. The selective hydrogenation is preferably carried out in the liquid phase or trickle phase using a fixed-bed hydrogenation catalyst. As hydrogenation catalysts, it is possible to use supported noble metal catalysts comprising palladium, platinum, silver, gold, rhodium, ruthenium, osmium or mixtures of these metals. Supported palladium-containing catalysts are particularly preferred as hydrogenation catalysts. A preferred hydrogenation catalyst used is described, for example, in EP-A 0 992 284. This comprises metals of groups 8, 9 and 10 of the Periodic Table, in particular ruthenium, rhodium, palladium and/or platinum, on an aluminum oxide support and, in addition, at least one metal of group 11 of the Periodic Table, preferably copper and/or silver. The amount of metal of group 8, 9 or 10 of the Periodic Table present in the catalyst is generally from 0.05 to 2% by weight, preferably from 0.1 to 0.5% by weight.

The selective hydrogenation can be carried out in one reactor or a plurality of reactors connected in series. The selective hydrogenation can, for example, be carried out in two stages. The temperature is usually in the range from 0° C. to 180° C. and the pressure is in the range from 2 to 50 bar. In one embodiment, the selective hydrogenation is carried out at a temperature of from 20 to 90° C. and a pressure in the range from 5 to 50 bar, with from 1 to 1.5 mol of hydrogen being added per mole of butadiene.

The stream e leaving the selective hydrogenation zone comprises predominantly 1-butene and 2-butene and in addition n-butane. In general, the stream e comprises from 20 to 50% by volume of 1-butene, from 50 to 80% by volume of 2-butene and from 0 to 10% by volume of n-butane. In addition, the stream e can contain small amounts of further gas constituents such as isobutane, isobutene and butadiene, generally in amounts of from 0 to 5% by volume, preferably from 0 to 1% by volume.

In a part F of the process, the stream e comprising 1-butene and 2-butene and a circulating stream g comprising 1-butene and 2-butene, which is obtained in a downstream part G of the process by isomerization of 2-butene, is introduced into a distillation zone. There, a desired product stream f1 consisting essentially of 1-butene is isolated so as to leave a 2-butene-containing stream f2.

The distillation zone generally consists of a distillation column which generally has from 30 to 80, preferably from 40 to 75, theoretical plates. Suitable columns are, for example, bubble cap tray columns, columns containing random packing, columns containing ordered packing or dividing wall columns. The reflux ratio is generally from 10 to 50. The distillation is generally carried out at a pressure of from 5 to 20 bar.

In the upper part of the column, preferably at the top of the column, the stream f1 consisting essentially of 1-butene is taken off. This generally comprises at least 90% by volume, preferably at least 95% by volume, of 1-butene and in addition up to 10% by volume, preferably up to 5% by volume, of further constituents such as n-butane, isobutane, isobutene, butadiene and 2-butene.

In the lower part of the column, preferably in the bottom fifth of the column, particularly preferably at a point from the bottom of the column up to at most 5 theoretical plates above the bottom of the column, a 2-butene-containing stream f2 is taken off. This stream f2 usually comprises from 55 to 95% by volume of 2-butene and in addition from 0 to 30% by volume of n-butane and from 0 to 15% by volume of 1-butene. A purge gas stream can be separated off from the stream f2 comprising 2-butene, in order to avoid accumulation of high boilers.

In a part G of the process, the 2-butene-containing stream f2 is introduced into an isomerization zone and an isomerization of 2-butene to 1-butene is carried out. Here, the 2-butene-containing stream f2 is passed over an isomerization catalyst. Suitable isomerization catalysts are basic catalysts or catalysts based on zeolites. In addition, the isomerization can also be carried out under hydrogenated conditions over catalysts comprising noble metals.

Suitable catalysts are alkaline earth metal oxides on aluminum oxide, as described in EP-A 0 718 036, mixed aluminum oxide/silicon oxide supports which have been doped with oxides of the alkaline earth metals, boron group metals, lanthanides or elements of the iron group, as described in U.S. Pat. No. 4,814,542, or gamma-aluminum oxide doped with alkali metals, as described in JP 51/108691. Further suitable catalysts are manganese oxide on aluminum oxide, as described in U.S. Pat. No. 4,289,919, magnesium oxide, alkali metal oxide and zirconium oxide dispersed on an aluminum oxide support, as described in EP-A 0 234 498, and also aluminum oxide catalysts which further comprise sodium oxide and silicon dioxide, as described in U.S. Pat. No. 4,229,610.

Suitable zeolite-based catalysts are described in EP-A 0 129 899. Also suitable are molecular sieves exchanged with alkali metals or alkaline earth metals, as described in U.S. Pat. No. 3,475,511, aluminosilicates, as described in U.S. Pat. No. 4,749,819, and also zeolites in the alkali metal or alkaline earth metal form, as described in U.S. Pat. No. 4,992,613, and those based on crystalline borosilicates, as described in U.S. Pat. No. 4,499,326.

The catalysts are usually used in a fixed bed, fluidized bed or moving bed. The isomerization is preferably carried out using a fixed-bed reactor through which the mixture to be isomerized flows continuously. Suitable reactors are tube reactors, shell-and-tube reactors, coil reactors or helical reactors. The isomerization temperature is generally from 100 to 700° C., preferably from 200 to 500° C. The pressure is generally from 1 to 30 bar, preferably from 3 to 20 bar.

A circulating gas stream g whose 2-butene content is from 5 to 30% by volume lower than that of the stream f2 is obtained. In general, the stream f2 comprises from 8 to 25% by volume of 1-butene, from 45 to 90% by volume of 2-butene and from 0 to 30% by volume of n-butane. The circulating gas stream g is fed together with the stream e comprising 1-butene and 2-butene into the distillation zone. A purged gas stream can be separated off from the circulating gas stream g. This can be recirculated to the dehydrogenation zone.

EXAMPLE

A feed gas stream a of 22 857 kg/h of n-butane is fed together with 1965 kg/h of oxygen and 14 735 kg/h of steam into a dehydrogenation reactor and subjected at 650° C. to an autothermal nonoxidative catalytic dehydrogenation.

A product gas stream b having the following composition is obtained (all percentage figures below are % by mass): n-butane 39.9%, isobutane 0.3%, 1-butene 9.3%, cis-2-butene 7.1%, trans-2-butene 9.6%, isobutene 0.3%, butadiene 4.8%, propane 0.1%, propene 0.7%, water vapor 24.4%, $CO_2$ 1.5%, CO 0.3%, oxygen 0.2%, hydrogen 1.1%, ethane 0.2%, ethene 0.1%, methane 0.1%.

Water vapor (15 937 kg/h) is condensed out from the product gas stream b, and low-boiling secondary components ($CO_2$ 953 kg/h, CO 178 kg/h, $O_2$ 101 kg/h, $H_2$ 705 kg/h, ethane 114 kg/h, ethene 84 kg/h, methane 66 kg/h, propane 90 kg/h, propene 443 kg/h) are subsequently separated off.

The remaining $C_4$ product gas stream c is subsequently separated in an extractive distillation into a recycle stream d1 consisting essentially of n-butane (26 125 kg/h) which is recirculated to the dehydrogenation reactor and a stream d2 consisting essentially of n-butane, 1-butene, 2-butene and butadiene (20 410 kg/h).

The composition of the recycled stream d1 is as follows: n-butane 93.5%, isobutane 0.7%, 1-butene 1.7%, cis-2-butene 1.3%, trans-2-butene 1.8%, butadiene 0.9%.

The composition of the stream d2 is as follows: n-butane 7.8%, isobutane 0.1%, 1-butene 27.6%, cis-2-butene 21.2%, trans-2-butene 28.4%, isobutene 0.8%, butadiene 14.19%.

The stream d2 is subsequently fed at a rate of 108 kg/h into a selective hydrogenation zone and subjected to a selective hydrogenation. A stream e (20 518 kg/h) having the following composition is obtained: n-butane 7.8%, isobutane 0.1%, 1-butene 36.4%, cis-2-butene 23.8%, trans-2-butene 31.1%, isobutene 0.8%, butadiene 0.01%.

In the subsequent isomerization/distillation, a desired product stream f1 (17 018 kg/h) consisting essentially of 1-butene and a stream f2 (3500 kg/h) consisting of 2-butene are obtained.

The desired product stream f1 has the following composition: n-butane 3.0%, isobutane 0.1%, 1-butene 95.9%, 2-butene 0.1%, isobutene 0.9%, butadiene 0.012%.

The stream f2 has the following composition: 31.4% n-butane, 4.7% 1-butene, 63.9% cis-2-butene.

The invention claimed is:

1. A process for preparing 1-butene from 1-butane, which comprises:
    A) providing a n-butane-containing feed gas stream a;
    B) introducing the n-butane-containing feed gas stream a into at least one dehydrogenation zone and nonoxidative catalytic dehydrogenation of n-butane to give a product gas stream b comprising n-butane, 1-butene, 2-butene, butadiene, hydrogen, low-boiling secondary constituents and possibly water vapor;
    C) removing hydrogen, the low-boiling secondary constituents and, if appropriate, water vapor to give a $C_4$ product gas stream c consisting essentially of n-butane, 1-butene, 2-butene and butadiene;
    D) separating the $C_4$ product gas stream c into a recycle stream d1 consisting essentially of n-butane and a stream d2 comprising 1-butene, 2-butene and butadiene by extractive distillation, and recirculating the recycle stream d1 consisting essentially of n-butane to the dehydrogenation zone;
    E) introducing the stream d2 comprising 1-butene, 2-butene and butadiene into a selective hydrogenation zone, and selective hydrogenating butadiene to 1-butene and/or 2-butene to give a stream e comprising 1-butene and 2-butene;
    F) introducing the stream e comprising 1-butene and 2-butene and a circulating stream g comprising 1-butene and 2-butene into a distillation zone, and isolating a desired product stream f1 consisting essentially of 1-butene to leave a 2-butene-containing stream f2; and
    G) introducing the 2-butene-containing stream f2, if appropriate after a purge gas stream has been separated off, into an isomerization zone and isomerization of 2-butene to 1-butene so as to give a circulating stream g comprising 1-butene and 2-butene, and recirculating, if appropriate after a purge gas stream has been separated off from the circulating gas stream g, the circulating gas stream g to the distillation zone.

2. The process according to claim 1, wherein the nonoxidative, catalytic dehydrogenation is carried out as an autothermal dehydrogenation.

3. The process according to claim 1, wherein the extractive distillation is carried out using an N-methylpyrrolidone/water mixture as an extractant.

4. The process according to claim 1, wherein the low-boiling secondary constituents are separated off by a high-boiling solvent in an absorption/desorption cycle.

5. The process according to claim 2, wherein the extractive distillation is carried out using a N-methylpyrrolidone/water mixture as an extractant.

6. The process according to claim 2, wherein the low-boiling secondary constituents are separated off by a high-boiling solvent in an absorption/desorption cycle.

7. The process according to claim 3, wherein the low-boiling secondary constituents are separated off by a high-boiling solvent in an absorption/desorption cycle.

* * * * *